United States Patent
Orsini et al.

(10) Patent No.: US 9,459,208 B2
(45) Date of Patent: Oct. 4, 2016

(54) DUCT DETECTOR WITH REMOTE AIRFLOW TEST CAPABILITY

(71) Applicant: SimplexGrinnell LP, Westminster, MA (US)

(72) Inventors: Todd F. Orsini, Sterling, MA (US); Donald D. Brighenti, Westminster, MA (US); Anthony J. Capowski, Westford, MA (US)

(73) Assignee: TYCO FIRE & SECURITY GMBH, Neuhausen am Rheinfall (CH)

( * ) Notice: Subject to any disclaimer, the term of this patent is extended or adjusted under 35 U.S.C. 154(b) by 379 days.

(21) Appl. No.: 14/046,157

(22) Filed: Oct. 4, 2013

(65) Prior Publication Data
US 2015/0096351 A1   Apr. 9, 2015

(51) Int. Cl.
   *G01N 21/53*    (2006.01)
   *G08B 29/14*    (2006.01)
   *G08B 17/107*   (2006.01)
   *G08B 17/113*   (2006.01)

(52) U.S. Cl.
   CPC ............ *G01N 21/53* (2013.01); *G08B 29/145* (2013.01); *G08B 17/107* (2013.01); *G08B 17/113* (2013.01)

(58) Field of Classification Search
   CPC ... G01N 21/53; G08B 17/107; G08B 29/145
   See application file for complete search history.

(56) References Cited

U.S. PATENT DOCUMENTS

| | | | | |
|---|---|---|---|---|
| 4,714,347 A * | 12/1987 | Cole | ................... | G08B 17/107 356/339 |
| 4,758,733 A * | 7/1988 | Mochizuki | ........... | G08B 17/107 250/574 |
| 4,851,819 A * | 7/1989 | Kawai | ................ | G08B 17/107 250/574 |
| 5,021,677 A * | 6/1991 | Igarashi | ............... | G08B 17/107 250/574 |
| 5,430,307 A * | 7/1995 | Nagashima | .......... | G08B 17/107 250/574 |
| 5,440,145 A * | 8/1995 | Cole | ................... | G01N 21/274 250/237 R |
| 5,625,346 A | 4/1997 | Shim et al. | | |
| 5,917,417 A * | 6/1999 | Girling | ................. | G01N 21/53 250/573 |

(Continued)

FOREIGN PATENT DOCUMENTS

EP   2645346 A2   2/2013
WO  2005071390 A1   8/2005

*Primary Examiner* — Lisa Caputo
*Assistant Examiner* — Punam Roy

(57) ABSTRACT

A device and method for facilitating convenient measurement of airflow in a duct detector. The device may include a detector assembly and an airflow sensor mounted within the detector assembly. The airflow sensor may be coupled to a remote control device, such as via control circuitry. A method for testing airflow in the duct detector may be performed by measuring airflow in the detector assembly, generating a signal that corresponds to the measured airflow in the detector assembly, and determining whether the generated signal exceeds a predetermined threshold signal level. If the generated signal does not exceed the threshold signal level, alarms may be activated and/or blowers in a ventilation system may be deactivated.

19 Claims, 3 Drawing Sheets

(56) References Cited

U.S. PATENT DOCUMENTS

| | | | | |
|---|---|---|---|---|
| RE37,353 E | * | 9/2001 | Kreikebaum | G01N 1/2273 250/576 |
| 7,034,702 B2 | * | 4/2006 | Thomas | G08B 17/107 340/628 |
| 7,834,755 B2 | * | 11/2010 | Butalla, III | G08B 17/10 340/506 |
| 8,289,177 B2 | * | 10/2012 | Bohanon | G08B 29/24 250/573 |
| 9,157,854 B2 | * | 10/2015 | Matsukuma | G01N 21/53 |
| 2004/0257235 A1 | * | 12/2004 | Right | F24F 11/0086 340/628 |
| 2005/0030172 A1 | | 2/2005 | Right et al. | |
| 2008/0117065 A1 | * | 5/2008 | Lang | G08B 17/10 340/628 |
| 2009/0051552 A1 | * | 2/2009 | Chabanis | G08B 17/107 340/584 |
| 2010/0039645 A1 | * | 2/2010 | Ajay | G01N 15/06 356/341 |
| 2011/0057794 A1 | * | 3/2011 | Egawa | G08B 25/009 340/540 |
| 2013/0239659 A1 | | 9/2013 | Brighenti et al. | |

\* cited by examiner

DUCT DETECTOR WITH REMOTE AIRFLOW TEST CAPABILITY

FIELD OF THE DISCLOSURE

The disclosure relates generally to smoke sensing systems, and more particularly to a device and method for facilitating convenient testing of smoke sensing systems within an air duct.

BACKGROUND OF THE DISCLOSURE

Air handling systems, such as heating, ventilation, and air conditioning (HVAC) systems, are ubiquitous in modern building infrastructure. It is often necessary to monitor air that flows through such air handling systems for the presence of impurities that may pose a threat to the health and well-being of a building's occupants. For example, it is common to monitor the levels of oxygen, carbon monoxide, particulate, and smoke in the air that flows through a building's air handling system. Such monitoring is typically facilitated by so-called "duct detectors" that are installed at various locations throughout a building's ductwork.

Unlike conventional smoke detectors and other point detectors that are commonly mounted to ceilings or walls within a building and that function by passively sensing convection currents of ambient gas, a duct detector includes a detector assembly encased in a sealed housing mounted to the exterior of a duct. An inlet conduit that is in fluid communication with the interior of the detector housing extends into the duct to gather a sample of air flowing therethrough. The gathered air enters the detector housing, passes through a filter screen that catches large particulate, flows through the detector assembly, and exits the detector housing through an exhaust conduit. In other duct detector embodiments, the detector housing, inlet conduit, and exhaust conduit are omitted, and the detector assembly is mounted within a duct, directly in the path of air flowing therethrough. In either case, the duct detector continuously samples and analyzes air that flows through a duct. If certain properties of the sampled air exceed or fall below predetermined limits, the duct detector may activate an alarm, and/or may deactivate blowers that drive air through the air handling system to mitigate the further spread of unsuitable air throughout a building.

As will be appreciated, performance of such duct detectors can degrade over time due to, for example, the clogging of the detector assembly filter screen by accumulated particulate. As such, governmental agencies often require that duct detectors be periodically tested to demonstrate proper functionality. Such testing is typically performed manually by a technician or other individual using an airflow meter or a pressure-differential meter to measure airflow through a detector hosing (in the case of an externally-mounted duct detector) or through a duct (in the case of an internally-mounted duct detector).

A problem commonly associated with the manual testing of airflow in duct detectors is that duct detectors are often installed in elevated locations, sometimes above ceilings, with few surrounding structures capable of supporting the weight of an individual during testing. Detectors that are located in such areas offer poor accessibility, rendering the task of airflow testing highly inconvenient and even hazardous. Moreover, while conventional manual testing techniques are capable of measuring the amount of air flowing through a duct detector housing (in the case of an externally mounted duct detector) or through a duct at a location adjacent a detector assembly (in the case of an internally mounted duct detector), such measurements may not be indicative of the amount of air that flows through the detector assembly itself. For example, a manually-administered airflow test may indicate that an acceptable amount of air is flowing through a detector housing even if the filter screen of the detector assembly within the housing has become excessively clogged with particulate that prevents a sufficient amount of air from flowing through the detector assembly.

SUMMARY OF THE DISCLOSURE

In view of the forgoing, a device and method for facilitating safe, convenient, and accurate airflow testing of a duct detector is disclosed. In particular, a duct detector is disclosed which incorporates remote airflow testing capability.

An exemplary duct detector (also referred to as a particulate detector) in accordance with the present disclosure may include a detector assembly including an airflow sensor mounted within the detector assembly for detecting particulate in air flowing therethrough. The airflow sensor may be coupled to a remote control device, such as via control circuitry.

A method for testing airflow in a duct detector is also disclosed. The method may include: measuring airflow in a detector assembly using an airflow sensor, generating a signal that corresponds to the measured airflow in the detector assembly, and determining whether the generated signal exceeds a predetermined threshold signal level. If the generated signal does not exceed the threshold signal level, alarms may be activated and/or blowers in a ventilation system may be deactivated.

BRIEF DESCRIPTION OF THE DRAWINGS

By way of example, a specific embodiment of the disclosed device will now be described, with reference to the accompanying drawings, in which.

DETAILED DESCRIPTION

Figure 1:
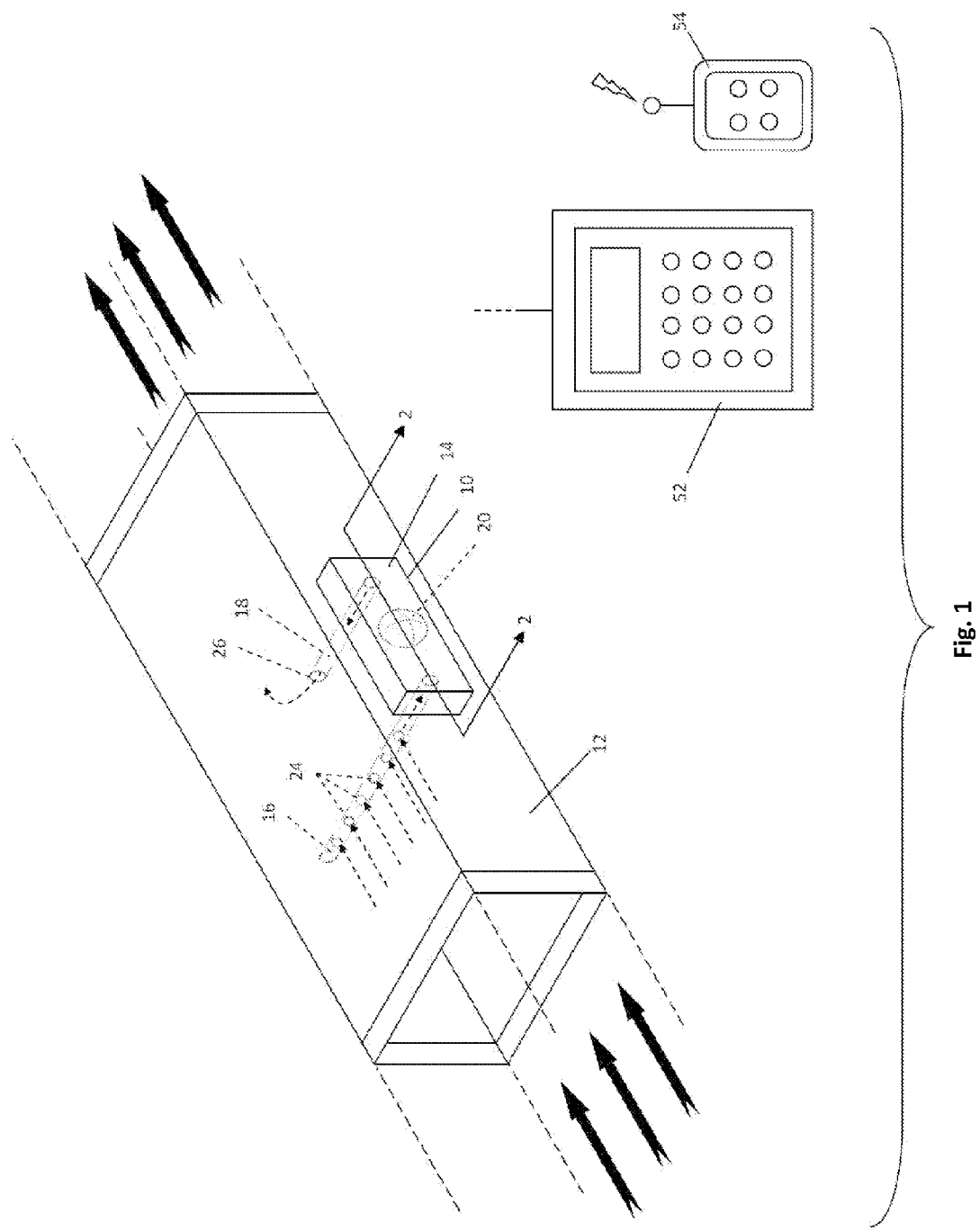
FIG. 1 is a transparent perspective view illustrating the disclosed duct detector installed on a section of duct.

Referring to FIG. 1, an improved duct detector 10 for facilitating convenient testing of airflow therethrough is shown operatively installed on an exemplary air flow duct 12. It is to be understood that the particular duct 12 is shown by way of example only, and is meant to be representative of any type of duct, such as may be commonly found in a variety of different buildings, and that the duct detector 10 can be employed in the manner described below in numerous other duct configurations. For example, the size and shape of the duct 12 can be varied with little or no effect on the functionality of the duct detector 10.

For the sake of convenience and clarity, terms such as "front," "rear," "top," "bottom," "upstream," "downstream," "inwardly," and "outwardly," will be used herein to describe the relative placement and orientation of the duct detector 10 and its various components, all with respect to the geometry and orientation of the duct detector 10 as it appears in FIG. 1. Particularly, the term "upstream" shall refer to a position nearer the lower left corner of FIG. 1 and the term "downstream" shall refer to a position nearer the upper right corner of FIG. 1. The large arrows shown in FIG. 1 therefore indicate movement in the downstream direction.

Figure 2:
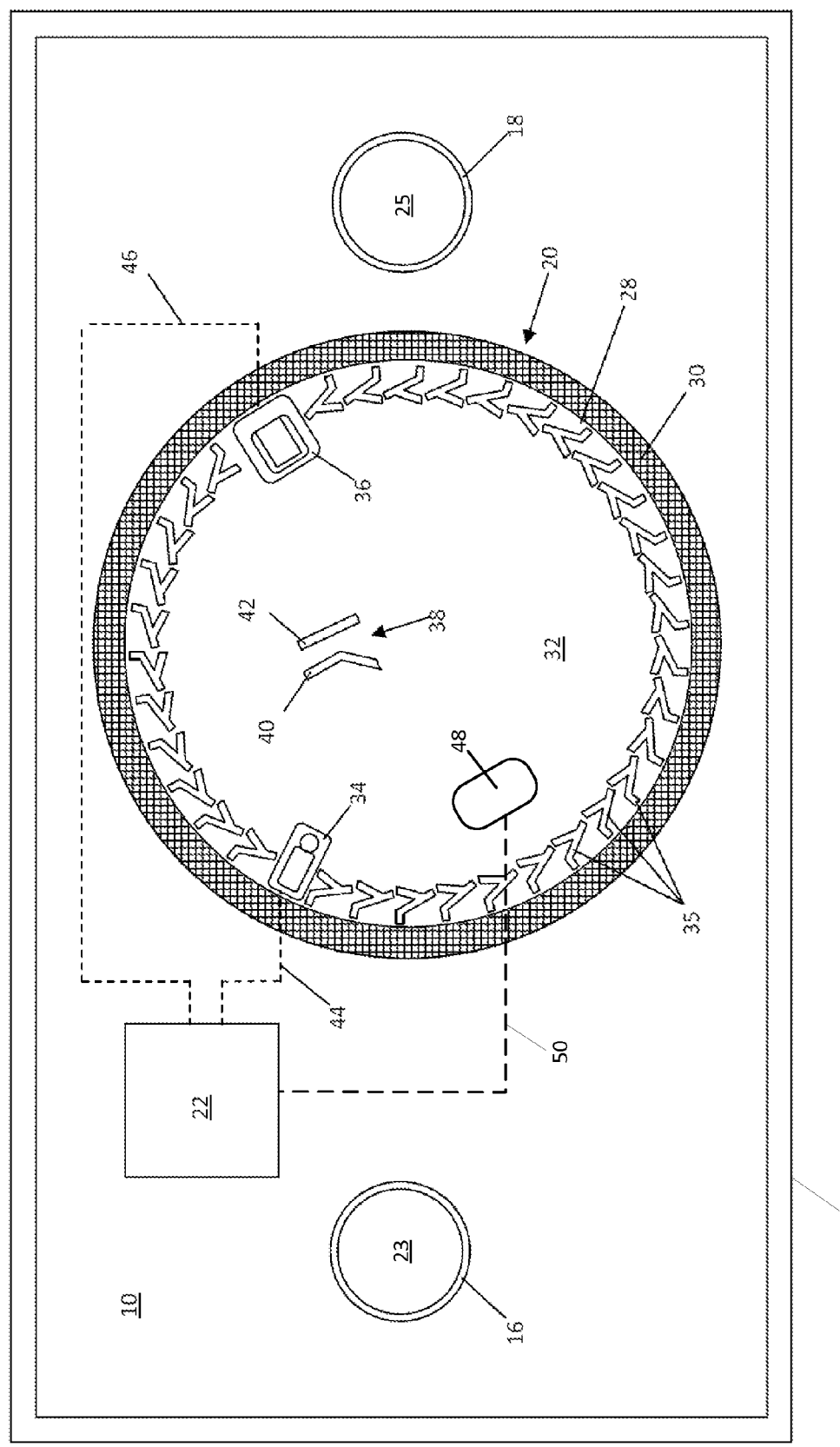
FIG. 2 is a cross-section view of the duct detector of FIG. 1, taken along line 2-2 of FIG. 1.

Referring to FIGS. 1 and 2, the duct detector 10 may include a main housing 14, an inlet conduit 16, an exhaust conduit 18, a detector assembly 20, and control circuitry 22. The main housing 14 may be a hollow body that houses the detector assembly 20 and the control circuitry 22. The inlet conduit 16 may be an elongated, tubular member that extends from an aperture 23 in the rear of the main housing 14 and has a hollow interior that is in fluid communication with the interior of the main housing 14. A series of apertures 24 can be provided in the inlet conduit 16 for allowing air to flow into the inlet conduit 16. The exhaust conduit 18 may be similar to the inlet conduit 16 and may be an elongated tubular member that extends from an aperture 25 in the main housing 14 and may have a hollow interior in fluid communication with the interior of the main housing 14. The exhaust conduit 18 may extend from the housing 14 on the opposite lateral side of the detector assembly 20 relative to the inlet conduit 16. An aperture 26 can be formed in the exhaust conduit 18, for example at its distal end, for allowing air to flow out of the exhaust conduit 18.

Referring to FIG. 2, the detector assembly 20 may be mounted to a wall of the main housing 14 intermediate the inlet conduit 16 and the exhaust conduit 18, and may include an assembly housing 28, a filter screen 30, a detector chamber 32, a light emitter 34, a light detector 36, and a septum 38. The assembly housing 28 may be a generally dome-shaped member formed by a plurality of angular labyrinth members 35. The labyrinth members 35 define a plurality of tortuous pathways between the interior and exterior of the assembly housing 28 that prevent some or all ambient light from entering the detector chamber 32, while simultaneously allowing ambient air to enter and exit the detector chamber 32.

The filter screen 30 of the detector assembly 20 may be formed of metal, plastic, or various composite materials and may be located radially outward of, and immediately adjacent to, the labyrinth members 35, thereby surrounding the assembly housing 28. The filter screen 30 may serve to prevent large particulate from entering and potentially clogging the labyrinth members 35 and detector chamber 32 while simultaneously allowing ambient air to enter and exit the detector chamber 32.

The light emitter 34 and light detector 36 may be mounted within the detector chamber 32, and in one embodiment they are embedded within the assembly housing 28, in an opposing relationship (i.e. on opposite lateral sides of the detector chamber 32). In one embodiment the light emitter 34 and light detector 36 may emit and detect infrared (IR) light, respectively. It is contemplated that the emitter 34 and detector 36 can be configured to emit and detect any of a variety of other types of light, including, but not limited to, visible light and ultraviolet (UV) light. It is further contemplated that a variety of other detector technologies may be implemented instead of, or in addition to, the above-described photo detector configuration (i.e., the light emitter 34 and light detector 36). For example, the detector assembly 20 may additionally or alternatively be implemented using an ion detector, a carbon monoxide detector, a multi-wavelength detector, etc.

The septum 38 of the detector assembly 20 can be defined by one or more straight and/or angular walls, such as walls 40 and 42, positioned along a line between the emitter 34 and the detector 36. The septum 38 thereby prevents direct light waves projected by the emitter 34 from being received by the detector 36. The interior surfaces of the detector assembly 20 may not reflect light, or may be minimally reflective of light, thereby preventing light projected by the emitter 34 from being reflected to the detector 36 unless reflective foreign matter (e.g., smoke) is present in the detector chamber 32 (as described below).

The control circuitry 22 of the duct detector 10 may be electrically connected to the light emitter 34 and the light detector 36, such as by conductive elements 44 and 46, each of which is representative of one or more power and/or control wires. The control circuitry 22 may thereby provide power to, and may control the function of, the emitter 34 and the detector 36 in a predefined manner. For example, the control circuitry 22 may include a microcontroller or processor that periodically flashes the light emitter 34 according to a programmed schedule (e.g. every five seconds). The control circuitry 22 may also monitor output from the light detector 36 and generate an alarm signal if a hazardous condition is detected (described in greater detail below), thereby actuating an audible alarm or deactivating an HVAC blower system, for example. While the control circuitry 22 is shown and described as being an integral, onboard component of the duct detector 10, it is contemplated that some or all of the control circuitry 22 can be located external to the duct detector 10, such as in a fire panel and/or other centralized location.

The duct detector 10 may further include an airflow sensor 48 mounted within the detector chamber 32. As will be described in greater detail below, the airflow sensor 48 may be used to periodically measure airflow in the detector chamber 32. In one embodiment, the airflow sensor 48 may be a hot wire anemometer. However, it is contemplated that any other type of airflow sensing device, including, but not limited to, thermistors, resistance temperature detectors, and transistors or diodes with thermal sensitivity, can additionally or alternatively be implemented in the duct detector 10 without departing from the present disclosure.

The airflow sensor 48 may be connected to the control circuitry 22, such as by connective element 50, for receiving power and control signals therefrom, but this is not critical. It is contemplated the airflow sensor 48 can alternatively receive power and/or control signals from a separate and/or external source via wired or wireless connection. For example, it is contemplated that the airflow sensor 48 can receive power from the control circuitry 22, but can receive a manually-actuated control signal through hardwired connection to a remotely-located fire or control panel, such as fire panel 52 in FIG. 1, for activating and deactivating the airflow sensor 48. It is further contemplated that the airflow sensor 48 can receive power from the control circuitry 22 or the fire panel 52 through hardwired connection, and can receive a wireless control signal from a handheld or fixed-location remote control device, such as remote control device 54 in FIG. 1, such as via radio or infrared signal, or via Wi-Fi or Bluetooth connection. Of course, if such wireless control arrangements are implemented an appropriate wireless receiver may be incorporated into the control circuitry 22 of the duct detector 10. It is contemplated that the remote control device 54 may be a specialized (i.e., proprietary) device, or may be a conventional portable device such as a smartphone, tablet, or laptop provided with appropriate interface software.

In certain contemplated embodiments, the duct detector 10, and particularly the control circuitry 22, may be operably connected to an addressable fire alarm network via the fire panel 52. The duct detector 10 may thereby be associated with a unique address within the alarm network for facilitating identification thereof by the alarm panel 52 and enabling selective routing of command/control signals from the alarm panel 52 to the control circuitry 22. Such addressability of the duct detector 10 may additionally facilitate remote testing of the performance of the duct detector 10 as further described below.

Referring again to FIG. 1, the duct detector 10 is shown installed on a section of duct 12 in a conventional manner that will be familiar to those of ordinary skill in the art. Particularly, the main housing 14 of the duct detector 10 is mounted to the exterior of the duct 12, such as with mechanical fasteners. The inlet conduit 16 and exhaust conduit 18 extend from the rear of the main housing 14 through corresponding apertures of slightly larger diameter in the duct 12, with the inlet conduit 16 positioned upstream relative to the exhaust conduit 18 and the apertures 24 in the inlet conduit 16 directed upstream. In certain alternative embodiments of the present disclosure, it is contemplated that the main housing 14, inlet conduit 16, and exhaust conduit 18 of the duct detector 10 may be omitted, and that the detector assembly 20 may be mounted within the duct 12, directly in the path of air flowing therethrough. In such an alternative configuration, the control circuitry 22 may be disposed within a housing mounted to an exterior of the duct 12, for example.

The control circuitry 22 (FIG. 2) may be connected to a centralized power and control source, such as by a conventional, hardwired connection. For example, the control circuitry 22 can be connected to a centralized fire panel or control panel, such as fire panel 52, from which a building's HVAC system can be controlled. Other operative configurations are also contemplated, as will be understood by one of ordinary skill in the art, and thus they will not be further described herein.

During typical use, air from the downstream airflow in the duct 12 enters the inlet conduit 16 through the apertures 24 and is channeled into the main housing 14 (as indicated by the small arrows in FIG. 1). The air then enters and exits the detector chamber 32 through the labyrinth members 35 and the filter screen 30. Finally, the air exits the main housing 14 through the exhaust conduit 18 and is expelled back into the duct 12 through the aperture 26 (as indicated by the small arrows in FIG. 1) where it rejoins the downstream airflow.

As air flows through the assembly housing 28 in the manner described above, the control circuitry 22 periodically flashes the light emitter 34, such as at five second intervals, for example. Alternatively, the light emitter 34 can be continuously lit. If the air in the detector chamber 32 does not contain a threshold amount of particulate, little or no light projected by the emitter 34 will be reflected to the detector 36 due to the lack of reflective particulate. If, however, the air in the detector chamber 32 contains at least a threshold amount of particulate, light will be reflected by the particulate and will be received by the light detector 36. A greater amount of particulate will generally reflect a greater amount of light.

The light detector 36 may then transmit an electrical output signal to the control circuitry 22 that corresponds to the amount of light received by the detector 36. If the electrical signal generated by the light detector 36 exceeds a predetermined "trip level," the control circuitry 22 may determine, such as through the execution of a software program by a processor or hardwired or programmable circuitry in the control circuitry 22, that the particulate content in the airflow has reached an unacceptable level. The control circuitry 22 may then generate an output signal that may actuate an alarm and/or cause a blower system to be deactivated, for example. The occupants of a building may thereby be notified of the alarm condition and the further spread of unsuitable air may be mitigated.

As previously noted, over time performance of the duct detector 10 may degrade due to clogging of the inlet conduit 16, the outlet conduit 18, and/or the filter screen 30 caused by, for example, the gradual accumulation of dust. Such clogging may block the entry of air, and therefore particulate (e.g., smoke), into the detector chamber 32 that could otherwise cause an alarm condition. In extreme cases such a condition will prevent the duct detector 10 from generating an alarm signal even if an excessive amount of particulate is present in the duct 12. Thus, it is desirable to periodically test the airflow within the detector chamber 32 to ensure that air and particulate are able to flow therethrough at an appropriate rate. If insufficient air flow is detected, maintenance personnel can be alerted to clean the duct detector and/or sampling tubes.

Figure 3:
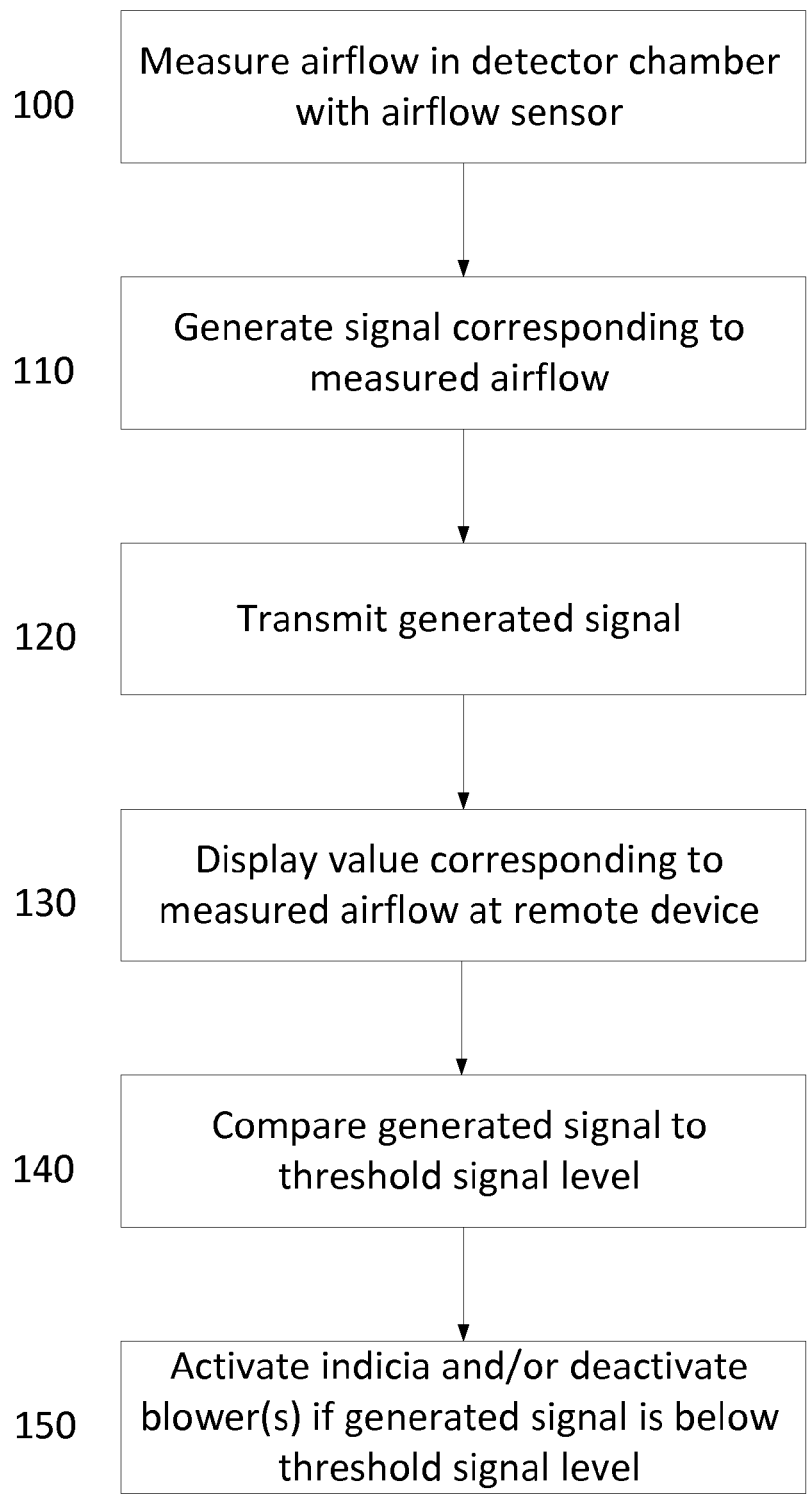
FIG. 3 is a flow diagram illustrating an exemplary method of testing air flow in the duct detector of FIGS. 1 and 2.

Referring now to FIG. 3, an exemplary method for executing the airflow test capability of the duct detector 10 will now be described. At step 100, a technician or other individual may initiate an airflow test of the duct detector 10 by activating the airflow sensor 48 (i.e., if such activation is necessary for obtaining a measurement from the airflow sensor 48) and/or by instructing the control circuitry 22 of the duct detector 10 to take a reading from the airflow sensor 48. This may be achieved by transmitting a control signal instructing such action to the control circuitry 22 through a wired or wireless control arrangement in the manner previously described. Alternatively or additionally, it is contemplated that the airflow test may be initiated automatically, such as by software residing in the fire panel 52, according to a predetermined schedule.

At step 110, the airflow sensor 48 may generate an electrical signal corresponding to the airflow measured in step 100. The electrical signal may be a current signal or a voltage signal, for example. At step 120, the electrical signal may be transmitted to the alarm panel 52.

At step 130 of the exemplary method, a value or indium corresponding to the airflow measured in step 100 may be presented on a display, such as at the fire panel 52 and/or on a display screen (not shown) of the handheld wireless device 54 shown in FIG. 1. A user may observe the displayed value and may determine whether the value meets or exceeds a predetermined threshold airflow value. If the measured airflow value is below the threshold airflow value, the inspector may perform or schedule maintenance or replacement of the duct detector 10, for example.

In addition or in alternative to step 130, the fire panel 52 may, at step 140 of the exemplary method, automatically compare the electrical signal generated by the airflow sensor 48 in step 110 to a predetermined threshold signal level. If the control fire panel 52 determines that the signal generated by the airflow sensor 48 does not meet or exceed the threshold signal level, the fire panel may, at step 150 of the exemplary method, generate an output signal that may activate an alarm or other indicia, thereby notifying personnel that the duct detector 10 should be inspected. The fire panel 52 may additionally or alternatively deactivate one or more blowers of an HVAC system, thereby mitigating the further transmission of potentially undetected contaminants.

It is contemplated that the above-described comparison of the electrical signal generated by the airflow sensor 48 and the subsequent activation of alarms and/or deactivation of blowers may additionally or alternatively be performed by the control circuitry 22 of the of the duct detector 10.

As will be appreciated, the disclosed duct detector 10 supports real time data collection to meet applicable government (e.g., fire code) requirements for supervision of device performance and capability, without requiring maintenance personnel to manually access the duct housing(s) to collect required data measurements.

As used herein, an element or step recited in the singular and proceeded with the word "a" or "an" should be understood as not excluding plural elements or steps, unless such exclusion is explicitly recited. Furthermore, references to "one embodiment" of the present invention are not intended to be interpreted as excluding the existence of additional embodiments that also incorporate the recited features. The terms "control circuit" and "processor" as used herein may refer to circuits and or components that include microprocessors, microcontrollers, microcomputers, programmable logic controllers, application specific integrated circuits, and other programmable circuits, and these terms are used interchangeably herein.

While certain embodiments of the disclosure have been described herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

The various embodiments or components described above may be implemented as part of one or more computer systems. Such a computer system may include a computer, an input device, a display unit and an interface, for example, for accessing the Internet. The computer may include a microprocessor. The microprocessor may be connected to a communication bus. The computer may also include memories. The memories may include Random Access Memory (RAM) and Read Only Memory (ROM). The computer system further may include a storage device, which may be a hard disk drive or a removable storage drive such as a floppy disk drive, optical disk drive, and the like. The storage device may also be other similar means for loading computer programs or other instructions into the computer system.

As used herein, the term "computer" may include any processor-based or microprocessor-based system including systems using microcontrollers, reduced instruction set circuits (RISCs), application specific integrated circuits (ASICs), logic circuits, and any other circuit or processor capable of executing the functions described herein. The above examples are exemplary only, and are thus not intended to limit in any way the definition and/or meaning of the term "computer."

The computer system executes a set of instructions that are stored in one or more storage elements, in order to process input data. The storage elements may also store data or other information as desired or needed. The storage element may be in the form of an information source or a physical memory element within the processing machine.

The set of instructions may include various commands that instruct the computer as a processing machine to perform specific operations such as the methods and processes of the various embodiments of the invention. The set of instructions may be in the form of a software program. The software may be in various forms such as system software or application software. Further, the software may be in the form of a collection of separate programs, a program module within a larger program or a portion of a program module. The software also may include modular programming in the form of object-oriented programming. The processing of input data by the processing machine may be in response to user commands, or in response to results of previous processing, or in response to a request made by another processing machine.

As used herein, the term "software" includes any computer program stored in memory for execution by a computer, such memory including RAM memory, ROM memory, EPROM memory, EEPROM memory, and non-volatile RAM (NVRAM) memory. The above memory types are exemplary only, and are thus not limiting as to the types of memory usable for storage of a computer program.

The invention claimed is:

1. A particulate detector for use in a ventilation duct, comprising:
   a detector assembly including an assembly housing, a filter screen, a labyrinth, a detector chamber, a light emitter, and a light detector;
   an airflow sensor disposed within the assembly housing; and
   control circuitry configured to deactivate a blower associated with a duct in which the particulate detector is installed if a signal generated by the airflow sensor does not exceed a predetermined threshold signal level.

2. The particulate detector of claim 1, wherein the airflow sensor is operatively coupled to a remote control device.

3. The particulate detector of claim 2, wherein the remote control device is coupled to the airflow sensor via a wired connection.

4. The particulate detector of claim 2, wherein the remote control device is coupled to the airflow sensor via a wireless connection.

5. The particulate detector of claim 2, wherein the remote control device is housed in a fixed-location panel within a building.

6. The particulate detector of claim 2, wherein the remote control device is a portable unit.

7. The particulate detector of claim 2, wherein the remote control device communicates with the airflow sensor through control circuitry associated with the duct detector.

8. The particulate detector of claim 1, wherein when the particulate detector is in a clean condition, airflow through the detector assembly is sufficient to cause the signal generated by the airflow sensor to exceed a predetermined threshold signal level.

9. The particulate detector of claim 1, wherein when the particulate detector is not in a clean condition, airflow through the detector assembly is insufficient to cause the signal generated by the airflow sensor to exceed a predetermined threshold signal level.

10. The particulate detector of claim 1, wherein the airflow sensor comprises an anemometer.

11. A method for testing airflow in a particulate detector comprising:
    measuring airflow in a detector assembly of the particulate detector using an airflow sensor;
    generating a signal that corresponds to the measured airflow in the detector assembly;
    determining whether the measured airflow exceeds a predetermined threshold airflow value; and
    automatically deactivating a blower associated with a duct in which the particulate detector is installed if the generated signal does not exceed the predetermined threshold signal level.

12. The method of claim 11, wherein determining whether the measured airflow exceeds a predetermined threshold airflow value comprises receiving the generated signal and comparing the generated signal to a predetermined threshold signal level.

13. The method of claim 12, further comprising automatically activating an indicium if the generated signal does not exceed the predetermined threshold signal level.

14. The method of claim 11, further comprising initiating testing of the airflow via a wireless control device.

15. The method of claim 11, further comprising initiating testing of the airflow via a fire panel.

16. A particulate detector for use in a ventilation duct, comprising a main housing;
    a detector assembly disposed within the main housing;
    an airflow sensor mounted within the detector assembly; and
    control circuitry configured to deactivate a blower associated with a duct in which the particulate detector is installed if a signal generated by the airflow sensor does not exceed a predetermined threshold signal level.

17. The particulate detector of claim 16, wherein the airflow sensor is coupled to a fire panel.

18. The particulate detector of claim 17, wherein the airflow sensor is coupled to the fire panel via a wired connection.

19. The particulate detector of claim 17, wherein the airflow sensor is coupled to the fire panel via a wireless connection.

\* \* \* \* \*